(12) United States Patent
Bruessow et al.

(10) Patent No.: US 7,435,434 B1
(45) Date of Patent: Oct. 14, 2008

(54) PHAGE RESISTANT BACTERIA

(75) Inventors: Harald Bruessow, La-Tour-de-Peilz (CH); Sacha Lucchini, Norwich (GB)

(73) Assignee: Nestec S.A., Vevey (CH)

( * ) Notice: Subject to any disclaimer, the term of this patent is extended or adjusted under 35 U.S.C. 154(b) by 494 days.

(21) Appl. No.: 10/070,038

(22) PCT Filed: Aug. 8, 2000

(86) PCT No.: PCT/EP00/07696

§ 371 (c)(1), (2), (4) Date: Jul. 17, 2002

(87) PCT Pub. No.: WO01/16329

PCT Pub. Date: Mar. 8, 2001

(30) Foreign Application Priority Data

Aug. 27, 1999 (GB) .................................. 9920431.5

(51) Int. Cl.
*C12N 1/20* (2006.01)
*C12N 7/01* (2006.01)
*A01N 63/00* (2006.01)

(52) U.S. Cl. .................. 426/61; 435/253.4; 435/235.1; 435/252.3; 424/93.6; 424/93.44

(58) Field of Classification Search ............. 435/252.3, 435/253.4, 235.1; 424/93.6, 93.44
See application file for complete search history.

(56) References Cited

FOREIGN PATENT DOCUMENTS

EP 0 183 469 A1 4/1986
EP 0 748 871 A1 12/1996

OTHER PUBLICATIONS

Document No. XP-002163736 Entitled: "A Short Noncoding Viral DNA Elements Showing Characteristics of a Replication Origin Confers Bacteriophage Resistance to *Streptococcus thermophilus*," *Virology* 250, 377-387 (1998).
Document No. XP002163737 Entitled: "Broad-Range Bacteriophage Resistance in *Streptococcus thermophilus* by Insertional Mutagenesis," *Virology* 275, 267-277 (2000).
Document No. XP-000673892 Entitled: "Efficient Insertional Mutagenesis in *Lactococci* and Other Gram-Positive Bacteria," *Journal of Bacteriology*, Feb. 1996, p. 931-935.

*Primary Examiner*—Rebecca E. Prouty
*Assistant Examiner*—Iqbal Chowdhury
(74) *Attorney, Agent, or Firm*—Bell, Boyd & Lloyd LLP (57) ABSTRACT

The invention relates to an *S thermophilus* bacterium which is resistant to attack by at least one bacteriophage, a method of production of the bacterium and a composition which comprises the bacterium. The bacterium comprises a modification of the Sfi21 prophage or the bacterial genome which disrupts expression of a gene which is essential to a bacteriophage, but not essential to the bacteria.

14 Claims, 6 Drawing Sheets

Figure 1

Plasmid tandem repeats →

```
                                      ISS1              Stop orf90      Start orf394
                                       ↓
2101  5'-CGTACTTATCAAGCAAGTAAGCTAGAAGAAAAG TAG GCTCCTAGG ATG AAGTAAGACAA
      3'-GCATGAATAGTTCGTTCATTCGATCTTCTTTTC ATC CGAGGATCC TAC TTTCATTCTGTT 2161  5'-TTAAGTGATAGTAAAGGTCTTTCTTACTTACATTTAGTAATGTTAAGTCTTTATGCAATT
      3'-AATTCACTATCATTTCCAGAAAGAATGAATGTAAATCATTACAATTCAGAAATACGTTAA
```

Figure 6

SEQUENCE LISTING

<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: DNA primer

<400> SEQUENCE: 1
aactgcagtc tcagctcaaa gggac                                          25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: DNA primer

<400> SEQUENCE: 2
ggaattctag ccgtgatgtt tttg                                           24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: DNA primer

<400> SEQUENCE: 3
ggaattcgac gcaattaaag accc                                           24

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: DNA primer

<400> SEQUENCE: 4
ccatcgatct gcttccaaaa tctcg                                          25

<210> SEQ ID NO 5
<211> LENGTH: 120
<212> TYPE: DNA
<213> ORGANISM: Streptococcus thermophilus
<220> FEATURE:
<223> OTHER INFORMATION: from position 22 to position 90 : sequence
      deleted in Sfi1-R7e and nucleotide C at position 22 is the
      pG+9ISS1 integration site

<400> SEQUENCE: 5
cgtacttatc aagcaagtaa gctagaagaa aagtaggctc ctaggatgaa agtaagacaa    60
ttaagtgata gtaaaggtct ttcttactta catttagtaa tgttaagtct ttatgcaatt   120

PHAGE RESISTANT BACTERIA

The present invention relates to a bacterium which is resistant to attack by at least one bacteriophage, a method of production of the bacterium and a composition which comprises the bacterium.

Within the context of this specification the word "comprises" is taken to mean "includes, among other things". It is not intended to be construed as "consists of only".

DNA bases and amino acids are represented herein by their standard one or three letter abbreviations as defined by the IUPAC Biochemical Nomenclature Commission.

It is well known that bacteria are placed in starters for production of milk products. They are used to optimise pH and flavour of the milk product. Indeed, production of cheese and dairy products has long relied on the fermentation of milk by bacteria. The bacteria are responsible for the development of acid, flavour production, and often coagulum characteristics in mesophilic dairy fermentations. Because efficient milk fermentations are dependent on the growth and activity of the bacteria, great care is exercised to prepare starter cultures that are highly active and uncontaminated with undesirable microorganisms or bacteriophages. However, the fermentation process itself is nonaseptic, occurring in open vats with a nonsterile medium, pasteurized milk. It is therefore highly susceptible to contamination by bacteriophages. For the majority of strains employed in commercial dairy fermentations, bacteriophages capable of halting bacterial growth and acid production can appear within one to two days after introducing the culture.

Historically, milk fermentation has relied on starter cultures having mixtures of lactic acid bacteria. The presence of bacteriophages or protection from them was either unknown or missing. Natural phage contamination in these cultures is thought to have established an equilibrium of evolving bacteriophages and phage-resistant bacterial variants. The cultures were highly variable in levels of acid production, but remained moderately active and could be used in small fermentation factories. More recently, the dairy industry has become more aware of starter culture failures due to bacteriophage infection and with an increasing demand for cultured milk products there is a need for an increase in both production capacity and process efficiency such that larger volumes of milk are processed and total processing time is shortened. This modernization of the industry has lead to an increased demand for uniform and rapid rates of acid production. However, the bacteria which may provide the best milk products may be highly susceptible to bacteriophage attack.

To cope with bacteriophage problems a number of methods have been developed to minimize phage infection in commercial milk fermentations. Through the use of concentrated cultures, aseptic bulk starter vessels and phage-inhibitory media (see, for example, U.S. Pat. No. 4,282,255), the starter culture can be protected from bacteriophage infection prior to vat inoculation. However, phage contamination cannot be prevented after introduction of the bacteria into the fermentation vessel.

Sandine, W. E., et al., J. Milk Food Technol. 35, 176 (1972) emphasized the need to isolate new bacterial strains for use in the dairy industry. Foremost among the criteria for selection of these strains was resistance to existing bacteriophages. It is now recognized that some strains of bacteria are not attacked by any phage when challenged with large collections of laboratory phage banks, or when used on a continuous, long-term basis in commercial fermentations. Some groups have reported the existence of bacteria that are not sensitive to bacteriophage attack. However, to date, only a limited number of phage-insensitive strains have been identified and studied for mechanism of phage resistance.

U.S. Pat. No. 4,530,904, discloses a method for protecting bacteria in general from different types of bacteriophage. The method involves transforming a bacterium with a recombinant DNA cloning vector which comprises a replicon that is functional in the bacterium, a gene that expresses a functional polypeptide (i.e., human growth hormone) in the bacterium, and a DNA segment which confers restriction and modification activity to the bacterium. The transformed bacterium is then cultured under large-scale fermentation conditions. This method is particularly adapted to fermentation procedures for the production of polypeptide products like growth hormone. Problems with this method are due to the fact that it relies on protection against phages provided by a restriction and modification (R/M) phage resistance mechanism cloned on a plasmid. There are two main problems. First, a plasmid has high metabolic costs and also instability problems (insert can be deleted, plasmid can be lost in abscence of an appropriate selection). Second, restriction and modification systems (R/M) can be powerful; they operate at varying levels of efficiency (EOP of $10^{-1}$-$10^{-6}$). But, the problem with them is that they allow some phages to escape restriction resulting in modified progeny virions. The modified phages can then infect a second host bearing an identical R/M system without being restricted (EOP=1.0).

Phage contamination is now considered to be a main cause of slow fermentation or complete starter failure. The lack of bacteria which survive adequately can result in milk products which do not have a desirable taste. Thus, a goal of scientists working to produce better milk products lies in providing bacteria which have all the characteristics associated with production of a good flavour and which are able to resist infection by bacteriophages.

A bacterium traditionally used in the production of milk products is *S. thermophilus*. It is particularly employed in the production of yogurt, mozzarella and Swiss type cheeses. One problem with *S. thermophilus* is that it is extremely sensitive to phage infection.

Little is known about natural phage resistance mechanisms of *S. thermophilus*. The bacterium was identified comparatively recently and, to date, very little data relating to the bacterium has been reported. In addition, it seems that *S. thermophilus* has fewer antiphage mechanisms than other bacteria eg *L. lactis*. In *Lactococcus lactis*, the major mesophilic starter of the dairy industry, natural phage-resistance mechanisms are abundant and usually encoded on conjugative plasmids. These have been used to construct food-grade phage resistance mechanisms into important industrial lactococcal starters. Information now obtained from phage genome analysis has shown no pausity in restriction sites as expected when phages are exposed to restriction/modification selection. Moreover, in contrast to *L. lactis*, where the majority of antiphage mechanisms have been linked to plasmids, *S. thermophilus* has a comparatively small number of plasmids.

Therefore, a need exists for a bacterium which has the characteristics associated with production of a good flavour and which is able to resist infection by bacteriophages. In addition, there is a need for a method of providing bacteria with resistance to phage attack thereby enabling strains to be selected on the basis of their ability to produce a good flavour rather than their ability to resist bacteriophages.

Spontaneous phage-insensitive mutants (PIM) can be selected by phage challenge and this approach has been applied to *S. thermophilus*. However, such mutants are usually slow acid producers and can also revert to phage sensitivity.

The present invention addresses the problems set out above.

SUMMARY OF THE INVENTION

Remarkably, molecular methods have now been exploited to create phage-resistant strains. A new and suprising approach based on inactivation of a bacterial host gene has proven successful in inactivation of prophages by bacterial gene inactivation by targeting them with food-grade plasmid(s). A second new and suprising approach is based on the protection provided by at least partial deletion of the Sfi21 prophage. Temperate phages usually code for superinfection immunity genes, which are quite effective in protecting the lysogen from superinfecfion by both temperate and lytic phages. In the case of phage Sfi21 the superinfection control appears to be mediated by two distinct genetic elements: orf 203, a superinfection immunity gene and orf 127, the phage repressor. A drawback is that Sfi21 lysogens continuously release infectious phage particles into the media, which could contaminate the factory and possibly prevent a later introduction of valuable starters susceptible to phage Sfi21. It has also been shown that temperate phages can be the source of lytic derivatives. Therefore, targeted deletions in the Sfi21 prophage were created and inserted in the known lysogenic starter Sfi1c16 to obtain a lysogen that would retain superinfection control, but has lost its capacity to produce infectious virions. Both approaches can provide powerful phage-resistant food-grade starters for industrial milk fermentation.

Consequently, in a first aspect the present invention provides a bacterium which is resistant to attack by at least one bacteriophage that comprises a modification of the Sfi21 prophage or the bacterial chromosome.

In a second aspect the invention provides a method of preparing a bacterium according to the invention which comprises the steps of disrupting the Sfi21 prophage or the bacterial chromosome by inserting or deleting a sufficiently large DNA sequence from the gene.

In a third aspect the invention provides a composition which comprises the bacterium according to the invention together with a carrier, adjuvant or diluent.

Preferably, an embodiment of the bacterium according to the present invention is a *S. thermophilus* bacterium. More preferably it is a strain of *S. thermophilus* selected from the group which consists of Sfi1 and Sfi1c16.

Preferably, an embodiment of the bacterium according to the invention comprises a modified bacterial chromosome. More preferably, the bacterial chromosome comprises additional DNA. Preferably, the additional DNA comprises the sequence of bases of ISS1 (see J. Bacteriol 178, 931-935 (1996)) or a functional equivalent thereof. More preferably the additional DNA is introduced to the bacterial chromosome in ORF 90 at a site which disrupts expression of a chorismate mutase chain A gene and/or disrupts expression of the down stream gene ORF 394; or in ORF 269 at a site which disrupts expression of an oxidoreductase gene.

Preferably, an alternative embodiment of the bacterium according to the present invention has a modified Sfi21 prophage which is modified by addition or deletion of sufficient DNA to disrupt expression of the prophage. More preferably the modification is a deletion. Even more preferably the modification comprises a deletion of at least part of ORF 1560.

Preferably, an embodiment of the method according to the invention comprises the step of modifying the bacterial chromosome to disrupt the expression of one or more genes which are required by a bacteriophage, but not essential for the bacterium. More preferably, the method includes the step of adding DNA to the chromosome. Preferably, the method comprises the step of adding DNA which comprises the sequence of bases of ISS1 (see J. Bacteriol 178, 931-935 (1996)) or a functional equivalent thereof. More preferably the method comprises the step of adding DNA to the bacterial chromosome in ORF 90 at a site which disrupts expression of a chorismate mutase chain A gene or in ORF 269 at a site which disrupts expression of an oxidoreductase gene.

Preferably, an alternative embodiment of the method according to the present invention comprises the step of modifying the Sfi21 prophage. Preferably it comprises the step of adding or deleting a sufficient amount of DNA to disrupt expression of the prophage. More preferably the modification is a deletion. Even more preferably the modification comprises the step of deleting at least part of ORF 1560.

Preferably, an embodiment of the composition according to the present invention comprises an embodiment of the bacterium together with a carrier, adjuvant or diluent. More preferably it is a starter culture or milk product.

An advantage of the present invention is that it provides a bacterium which is resistant to attack by bacteriophages.

Another advantage of the present invention is that it provides a bacterium which does not revert to bacteriophage sensitivity and the method by which it is produced is generally applicable.

Yet another advantage of the present invention is that it provides bacteria having such a high level of phage resistance that the obtained phage-resistant bacteria do not allow spontaneous development of mutated phages that could infect the bacteria. This is not the case for other phage resistance mechanisms. Thus, these bacteria should be protected over a long period before new phages develop, which could infect them.

Yet another advantage is that bacteria have been obtained which have resistance to attack by a broad range of phages. The wild type Sfi1 bacterial strain is extremely susceptible to phage attack. It can be infected by more than 25 different phages (normal strains are susceptible to 1 or 2 phages). In stark contrast, no phages were able to infect the mutated Sfi1 strains according to embodiments of the invention. It is important to stress that the stability of the bacteriophage resistance phenotype of chromosomally modified bacteria is in contrast to the weak resistance of bacteria that have plasmid encoded phage resistance mechanisms. Moreover, there are presently no known food-grade plasmids available that may be used to provide phage resistance in *S. thermophilus*.

Additional features and advantages of the present invention are described in, and will be apparent from, the detailed description of the presently preferred embodiments which are set out below with reference to the drawings in which:

DETAILED DESCRIPTION OF THE INVENTION

Without wishing to be bound by theory it is postulated that the presence of some bacterial genes are essential to phage development, but dispensable for bacterial growth in milk. In fact, it is now thought that bacteriophages depend on host factors in many steps of their life cycle, e.g. adsorption, DNA injection, replication and morphogenesis. Disruption of one of these factors is now considered to lead to a phage-resistant cell.

Having no knowledge of the S. thermophilus genome, random gene inactivation was carried out with the temperature sensitive plasmid pG+host9ISS1. The method is self-selective: after phage challenge non-resistant cells are eliminated and mutants leading to decreased bacterial fitness are outnumbered.

Materials and Methods

Strains, media, plasmids, and culture conditions were as follows. The E. coli strain 101 was propagated in LB broth or LB broth solidified with 1.5% (W/V) agar at 37° C. Liquid cultures were grown under agitation (240 rpm). S. thermophilus strains Sfi1, its lysogenic derivative Sfi1c16 (containing the Sfi21 prophage) and their transformants were cultivated at 42° C. either in M17 supplemented with 0.5% lactose (LM17), Belliker media or MSK. Erythromycin was used when required at a final concentration of 2 and 150 µg/ml for S. thermophilus and E. coli, respectively. The phages used in this study were obtained from the Nestle Culture Collection and propagated on their appropriate S. thermophilus strain in LM17 broth as described previously. Phage enumeration was achieved as described previously. For random insertion mutagenesis and directed mutagenesis, plasmids pG+host9ISS1 and pG+host9 have been used, respectively.

DNA Techniques

Phage purification, DNA extraction and purification, agarose gel electrophoresis, Southern blot hybridization, and DNA labelling were executed as described previously. The Qiaprep plasmid kit (Qiagen) was used for the rapid isolation of plasmid DNA from E. coli. Restriction enzymes and T4 ligase were purchased from Boehringer-Mannheim and used according to the supplier's instructions. E. coli was electrotransformated as outlined in the BioRad instruction manual. S. thermophilus was electroporated using the procedure described by Slos et al. The analysis of intracellular phage DNA, PCR and DNA sequencing have been performed as described previously.

Sequence Analysis

The Genetics Computer Group (University of Wisconsin) sequence analysis package was used to assemble and analyze the sequences. Nucleotide and predicted amino acid sequences were compared to those in commercially available databases (GenBank, release 109, EMBL, release 56; PIR-Protein, release 57; SWISS-PROT, release 36; and PROSITE, release 15.0) with FastA and BLAST programs (2). Prediction of transmembrane domains was performed using the TMpred program.

Construction of Plasmid for Site Directed Integration

To create a deletion in the Sfi21 prophage, the thermosensitive plasmid pG+host9AB1560, a derivative of pG+host9 has been created. Two fragments of approximately 500 bp, A and B, were chosen in the orf1560 on the prophage sequence at a distance of 2.4 kb so that a deletion of the same size would be created by homologous recombination. Fragment A was generated by PCR using phage Sfi21 DNA as a template and primers (5'-AACTGCAGT CTC AGC TCA AAG GGA C-3' and 5'-GGAATTCTA GCC GTG ATG TTT TTG-3') containing PstI and EcoRI restriction sites (underlined). Fragment B was generated by PCR using primers (5'-GGAATTCGA CGC AAT TAA AGA CCC-3' and 5'-CCATCGATC TGC TTC CAA AAT CTC G-3') containing EcoRI and ClaI restriction sites. Both clones were then cloned into pG+host9, so to be adjacent, generating the construct pG+host9AB1560. The construct was first generated into E. coli 101, then transformed into S. thermophilus Sfi1c16.

Transposition of pG+host9ISS1 and pG+host9AB1560 in the S. thermophilus Chromosome S. thermophilus Sfi1 and Sfi1c16 containing pG+host9ISS1 and pG+host9AB1560, respectively, were grown overnight in LM17 medium supplemented with 2 µg/ml of erythromycin. The saturated cultures were diluted 100-fold in LM17 medium containing 1 µg/ml of erythromycin and incubated 2 h at 30° C. The cultures were then shifted to 42° C. to eliminate free plasmids and grown to saturation. The frequency of integration per cell was estimated as the ratio of the number of $Em^R$ cells at 42° C. to the number of viable cells at 30° C. Integration of the plasmids was checked by Southern blot hybridization. To excise the transposed vectors, serial passages have been performed in LM17 broth without antibiotic.

Selection of Phage-Resistant Mutants

The culture containing the original population of Sfi1::pG+host9ISS1 integrants was diluted 100-fold in LM17 supplemented with 2 µg/ml of erythromycin and challenged with lytic phage Sfi19 at a M.O.I. of 5. The culture was then grown to saturation. The experiments were considered unsuccessful when no growth was observed after 48 h.

Figure 1:
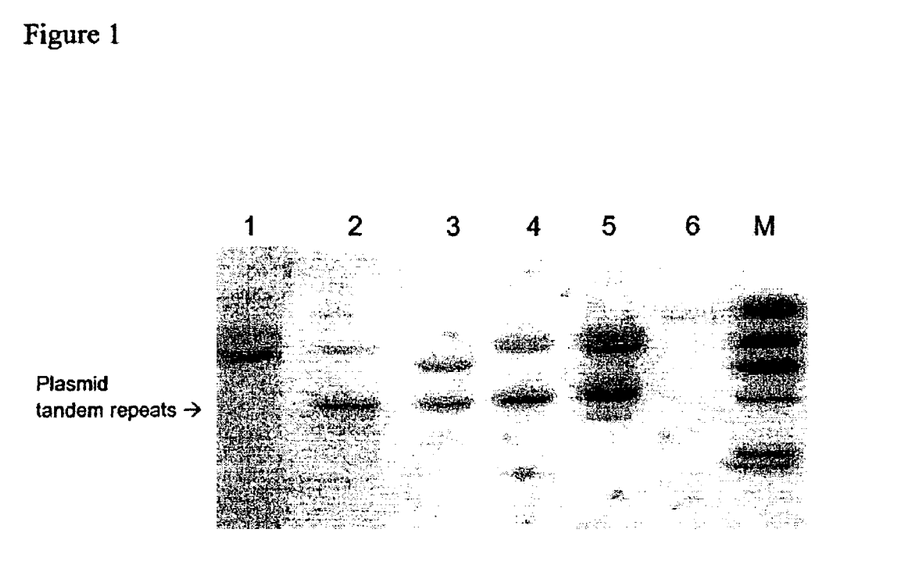
FIG. 1 shows results of a Southern blot of total DNA of phage resistant integrands. Lanes 1-5: phage resistant Sfi1::pG+host9ISS1. Lane 6: Sfi1. M: DNA marker (λ-DNA×HindIII). The blot was probed with radioactively marked pG+host9ISS1 plasmid and λ-DNA. Note: this figure is the combination of two independent blots (lane 1 has been added).

Individual phage-resistant colonies were isolated; their total DNA was extracted, and digested with EcoRI, and Southern blots were performed using the plasmid DNA as probe. Three different hybridization patterns were identified, corresponding to the Sfi1-R7 (lane 3), Sfi1-R24 (lane 1) and Sfi1-R71 (lanes 2, 4, 5) insertion mutants (FIG. 1).

Phage Adsorption Test

S. thermophilus cultures were grown in LM17 until an $OD_{600}$ of 0.6 was reached. Then phages were added at a M.O.I. of 1 and the cultures incubated at room temperature. Probes were taken immediately after phage addition and after 30 min. These probes were then filtered to remove the bacterial cells from the cultures. Phages left were then enumerated. The adsorption was calculated as phage counts at time 30 divided by the phage counts at time zero.

Results

Random mutagenesis of *S. thermophilus* Sfi1 was carried out. Starter strain Sfi1 was the best indicator cell. It is susceptible to about 25 of the 100 phages from the Nestle Culture Collection. This allows testing mutant starters against a broad range of phages.

Transposition of the plasmid could be achieved with a very high integration frequency, about 50% (see materials and methods). Integrants were randomly chosen on agar-plates and grown in liquid cultures. Their total DNA was then extracted to check by Southern blot hybridization the integration of the plasmid into the chromosome. Hybridization was performed on EcoRI digested chromosomal DNA using labelled pG+host9ISS1 as probe. All integrants showed signals corresponding to distinct chromosomal fragments (data not shown), confirming the integration of the plasmid and the randomness of the transposition.

Selection of Phage-Resistant Mutants

Integrants were challenged with the lytic phage Sfi19 (M.O.I.=5) to select for phage-resistant mutants. In presence of phage Sfi19 the Sfi1::pG+host9ISS1 culture showed a delayed growth, an $OD_{600}$ of 0.85 was only reached after 8 to 12 h of incubation in comparison with 3 h for the transformants in the absence of challenge phage. In contrast, no growth was observed for the parental Sfi1 starter after phage challenge ($OD_{600}$<0.02 after 48 h). In fact, in LM17 medium we consistently failed to obtain phage resistant mutants of starter Sfi1 after challenge with numerous phages.

Three mutants were selected and designated Sfi1-R7, Sfi1-R24 and Sfi1-R71.

Characterization of the Phage-Resistant Mutants

The 3 mutants were tested for phage resistance against 15 different *S. thermophilus* phages. In no case, phage plaques were observed suggesting in some cases efficiency of plating of $<10^{-7}$ (Table 1).

TABLE 1

| Phage | Sfi1 (pfu/ml) | Sfi1-R7 (pfu/ml) | Sfi1-R24 (pfu/ml) | Sfi1-R71 (pfu/ml) |
|---|---|---|---|---|
| Sfi21 | $6 \times 10^8$ | $<10^2$ | $<10^2$ | $<10^2$ |
| S69 | $7.2 \times 10^3$ | $<10^2$ | $<10^2$ | $<10^2$ |
| Sfi3J | $2 \times 10^8$ | $<10^2$ | $<10^2$ | $<10^2$ |
| St44A | $1 \times 10^8$ | $<10^2$ | $<10^2$ | $<10^2$ |
| S19 | $2 \times 10^8$ | $<10^2$ | $<10^2$ | $<10^2$ |
| S96 | $4 \times 10^7$ | $<10^2$ | $<10^2$ | $<10^2$ |
| St44 | $1 \times 10^8$ | $<10^2$ | $<10^2$ | $<10^2$ |
| St40 | $2 \times 10^5$ | $<10^2$ | $<10^2$ | $<10^2$ |
| Sfi18 | $2.7 \times 10^7$ | $<10^2$ | $<10^2$ | $<10^2$ |
| Sfi19 | $1.1 \times 10^9$ | $<10^2$ | $<10^2$ | $<10^2$ |
| St25 | $3 \times 10^8$ | $<10^2$ | $<10^2$ | $<10^2$ |
| St17 | $1 \times 10^8$ | $<10^2$ | $<10^2$ | $<10^2$ |
| S17 | $6 \times 10^8$ | $<10^2$ | $<10^2$ | $<10^2$ |
| H | $4.5 \times 10^3$ | $<10^2$ | $<10^2$ | $<10^2$ |
| F | $1 \times 10^4$ | $<10^2$ | $<10^2$ | $<10^2$ |

To get an indication of the stage at which phage development is blocked, phage-adsorption and phage DNA-replication tests were performed. The adsorption test was performed using Sfi19 on Sfi1 and the three mutants. After 30', 90% of the input phages adsorbed to Sfi1, 94% to Sfi1-R7, 91% to Sfi1-R24 and 87% to Sfi1-R71. This indicates that the mutation did not affect phage adsorption.

Figure 2:
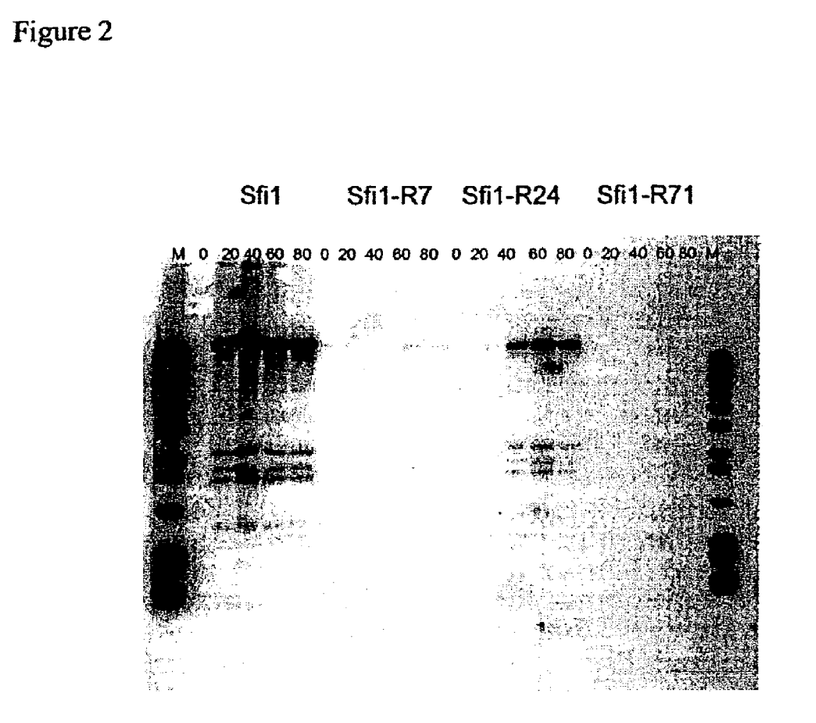
FIG. 2 shows the results of detection of intracellular phage DNA. The numbers correspond to the time in minutes after which samples have been taken (see Materials and Methods). The two lines marked with M correspond to the size marker (1 kb DNA Ladder, GibcoBRL).

DNA replication of phage Sfi19 in Sfi1 and the mutants was analyzed by determining the relative amount of intracellular phage DNA at different times during phage infection. In Sfi1 phage DNA was readily detected 20 min after infection (FIG. 2). The amount of DNA increased to a maximum after 40 min. Then a decrease was observed after 60 and 80 min, probably because of phage induced cell lysis. Phage DNA replication in the Sfi1-R24 mutant was delayed and decreased.

Figure 3:
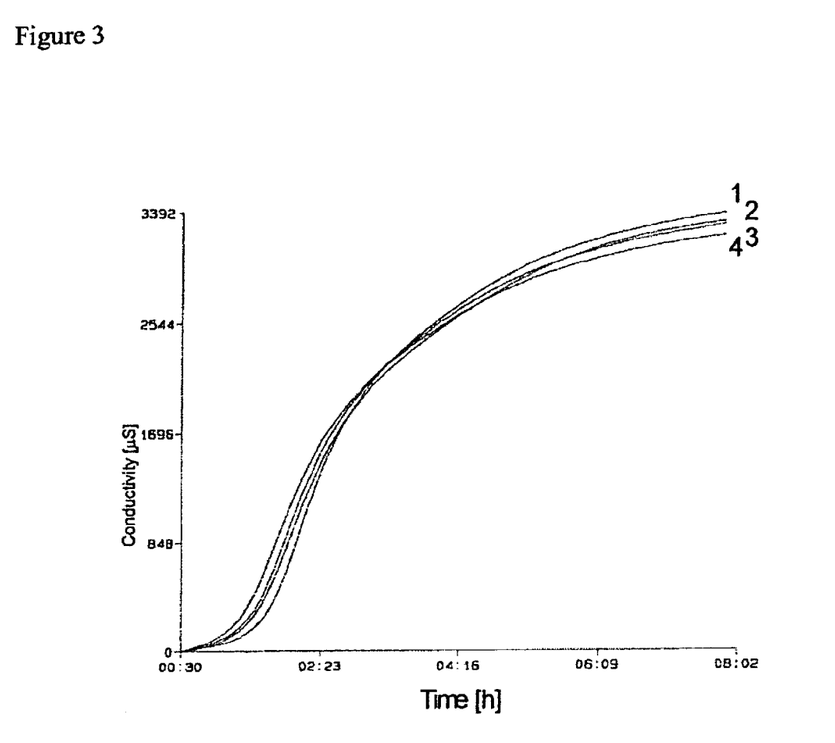
FIG. 3 shows growth curves of phage-resistant S. thermophilus strains compared to the parental strain. 1: Sfi1. 2: Sfi1-R7. 3: Sfi1-R71. 4: Sfi1-R24.

Phage DNA was detected only after 40 min reaching a maximum at 60 min. In the case of Sfi1-R7 and Sfi1-R71 no phage replication was observed. A very low and invariable level of phage DNA was detected by hybridization. This could represent the injected DNA of the infecting input phages or DNA from uninjected, but adsorbed input phages. The growth of the mutants was compared to that of the wild type strain in milk. This was done by measuring changes in impedance of the culture media (Rapid Automated Bacterial Impedance Technique, Don Whitley Systems). This system measures indirectly the transformation of a weak electrical conductor like the polar, but uncharged lactose into the electrically charged lactic acid during bacterial growth. The resulting curve (time vs. conductivity) can be correlated with both bacterial growth and acidification of the culture. All three mutants did not show significant differences in growth (and acidification) to the parental strain Sfi1 (FIG. 3).

Determination of the Site of Integration

Figure 4:
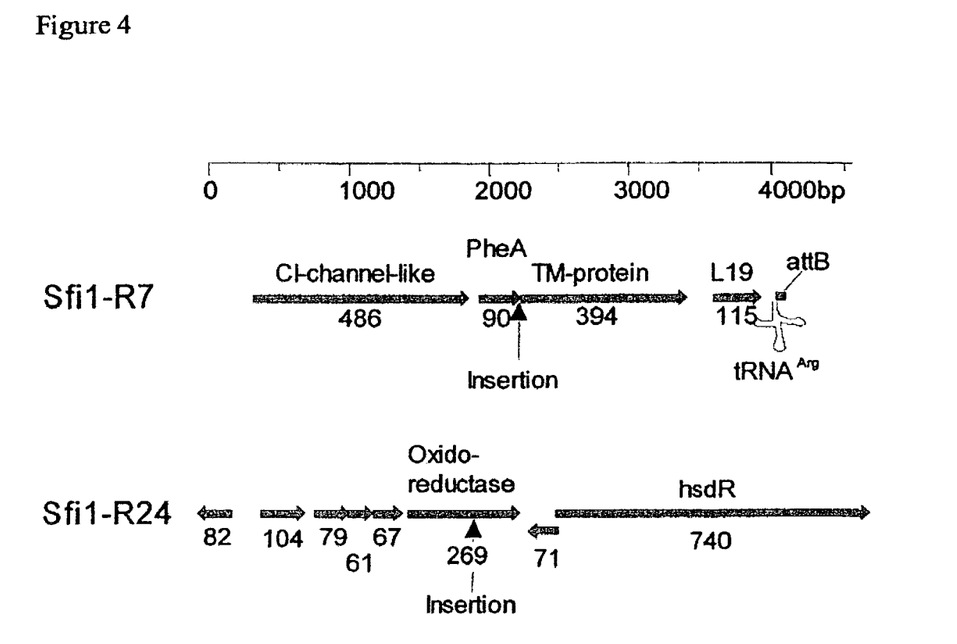
FIG. 4 shows sites of pG+host9ISS1 insertion in Sfi1-R7 and Sfi1-R24. Open arrows indicate the predicted open reading frames (orf). The numbers indicate the number of codons for each orf. When possible, a tentative function has been attributed to the predicted gene products.

The fragments adjacent to the insertion point were obtained by plasmid rescue as described by Maguin et al. for the Sfi1-R7 and Sfi1-R24 mutants. The approach was unsuccessful for Sfi1-R71. The regions flanking the pG+host9ISS1 insertion point were sequenced for the two mutants (FIG. 4).

In Sfi1-R7 the plasmid integrated in the last 4 amino acids of a putative chorismate mutase chain A gene (PheA), orf 90. This site of integration could also function as promoter region for the downstream orf 394. Orf 394 gene product shows similarities (26% identity) to a hypothetical conserved protein of *Methanococcus jannashii* (Accession number MJ0305). Orf 394 gp may be an integral protein since 9 strong transmembrane helices were predicted. Orf 115 gp encoded by a gene located directly downstream of orf 394, showed significant similarity to the ribosomal protein L19 from a number of bacteria (*Haemophilus influenzae, Salmonella typhimurium, Serratia marcescens, Synechocystis* sp.). A gene almost identical to a tRNAArg gene (anticodon CCU) follows this gene from *E. coli* and interestingly the phage attachment site attB for prophage integration. Upstream of orf 90 a gene we identified orf 486 (see FIG. 4), which encodes a further possible membrane protein. The deduced protein for this orf shows significant similarity (50% over 427 aa) to a hypothetical C1-channel-like protein from *E. coli* (Accession number P37019).

In Sfi1-R24 the pG+host9ISS1 insertion point was in a likely oxidoreductase involved in fatty acid biosynthesis (orf 269). The predicted protein showed 42% amino acid identity with an *E. coli* 3-oxoacyl-[acyl-carrier protein] reductase.

Interestingly, one fragment of an R-subunit of a type I restriction enzyme is located downstream orf 269. No database matches were found for the orfs upstream of orf 269.

Plasmid Excision.

Figure 5:
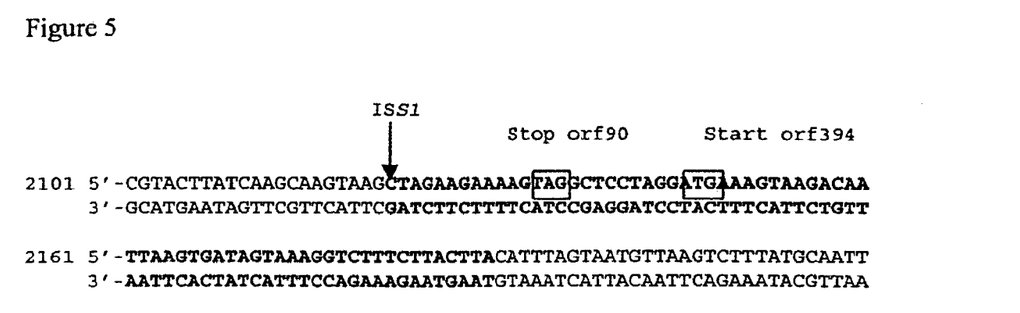
FIG. 5 shows deletion in Sfi1-R7e. The sequence deleted in Sfi1-R7e is in bold. The arrow indicates the pG+host9ISS1 integration site.

To obtain food-grade starter strains it is necessary to remove the erythromycin resistance gene present in the transformants. ISS1 undergoes replicative transposition which leads to an integrated plasmid vector flanked by two IS elements. Therefore, homologous recombination between this two copies of the IS element will entirely remove the plasmid and leave only a single copy of the IS element. To favor recombination, serial passages of the transformants were done in absence of antibiotic selection. Sfi1-14 lost the $Em^R$ phenotype after 29 passages (now Sfi1-R24e), Sfi1-R71 after 40 (Sfi1-R71e). Excision was easier with Sfi1-R24, because of the lack of tandem repeats (FIG. 1). Sfi1-R7Em$^S$ (Sfi1-R7e) could be obtained after 60 passages. Then, phage resistance was checked for the Em$^S$ mutants. In 2 cases (Sfi1-R24 and Sfi1-R71) the loss of the plasmid resulted in full reversion to phage sensitivity while Sfi1-R7e did retain its full phage resistance phenotype. This derivative lacked the plasmid sequence except for one ISS1 sequence. Sequencing of the flanking sequences of the remaining ISS1 showed in addition a 69 bp deletion which started at the IS transposition site and removed 3'-end of orf 90 and the first 15 codons of orf 394 (FIG. 5). Since two independently obtained Sfi1-R7e mutants showed the same deletion it is likely that the deletion has already occurred in the parental Sfi1-R7 mutant.

Deletion of Orf 1560 from the Sfi21 Prophage

Integration of pG$^+$host9AB1560 into the prophage was readily obtained (see materials and methods). Integration in the right site was checked by PCR. More than 50% of the integrands were shown to give a signal corresponding to the predicted size for homologous recombination events. Plasmid excision was obtained after 20 serial passages. Because the second homologous recombination can lead both to the wild type or the deletion mutant, PCR was used to test the Em$^S$ clones. As expected about 50% of the clones were deletion derivatives (Sfi1c16Δ1560).

Characterization of Sfi1c16Δ1560

To test if an essential gene of the phage had been inactivated the prophage of both Sfic16 and Sfi1c16Δ1560 was induced with 2 μg/ml of Mytomicin C. Sfic16 released 105 pfu/ml, Sfi1c16Δ1560 released no detectable infectious particles. Subsequently, it was checked whether the superinfection exclusion phenotype was preserved in the derivative lysogen.

TABLE 2

| Phage | Sfi1 (pfu/ml) | Sfi1c16 (pfu/ml) | Sfi1c16Δ1560 (pfu/ml) |
| --- | --- | --- | --- |
| Sfi18 | 7.4 × 10$^7$ | <10$^2$ | <10$^2$ |
| S96 | 9.8 × 10$^6$ | <10$^2$ | <10$^2$ |
| Sfi21 | 8.3 × 10$^7$ | <10$^2$ | <10$^2$ |
| Sfi19 | 1.6 × 10$^8$ | 8.8 × 10$^5$ | 1.7 × 10$^6$ |
| ST25 | 1.1 × 10$^8$ | 1.6 × 10$^7$ | 2.2 × 10$^7$ |
| ST17 | 6.5 × 10$^8$ | 1.2 × 10$^4$ | 1.3 × 10$^4$ |

Figure 6:
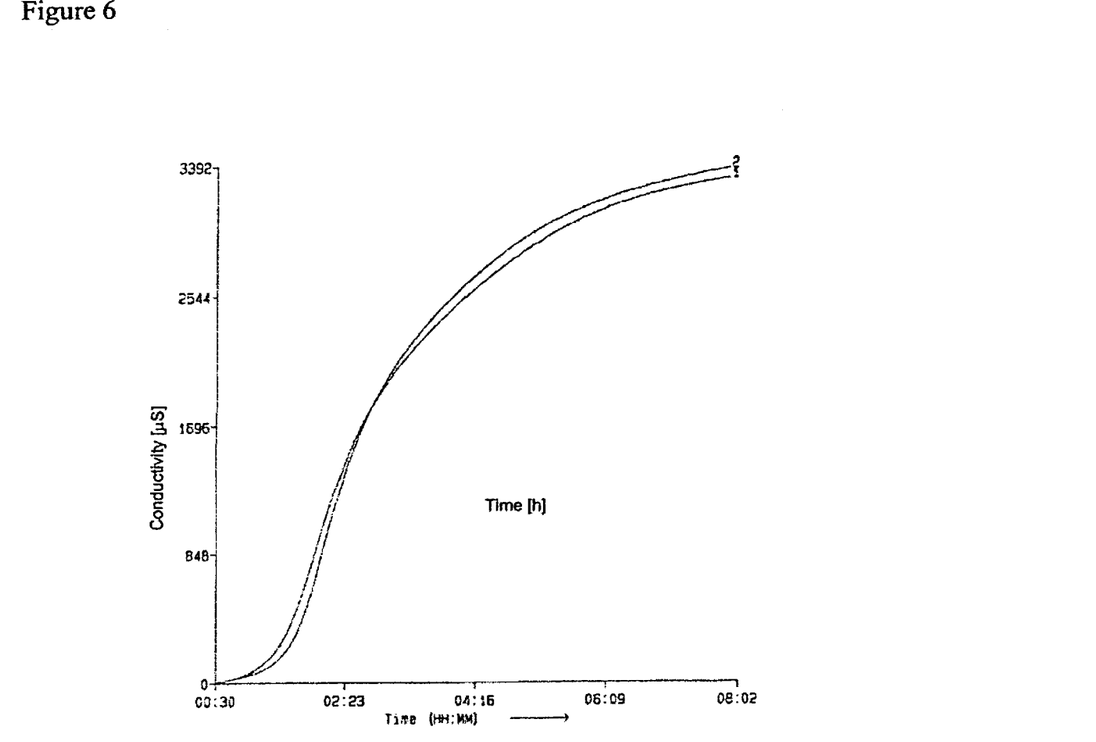
FIG. 6 shows growth curve of S. thermophilus Sfi1c16D1560 (2) compared to Sfi1c16 (1).

In fact, plaque assays demonstrated an identical phage exclusion phenotype in both with respect to suppression of phage infectivity expressed as efficiency of plating as well as in the range of different phages which were inhibited (Table 2). Growth curves of the lysogen and its deletion derivative were identical (FIG. 6).

The invention provides an increase in phage resistance of $S.$ $thermophilus$ starter strains. Random insertion of an integrative plasmid into the chromosome of $S.$ $thermophilus$ led to production of highly phage resistant (e.o.p.<10$^{-6}$) mutants.

The broad range of anti-phage activity of the Sfi1-R7 mutation suggests that the 15 phages, which were tested, have similar requirements for host factors; i.e. orf 90 and orf 394 gps. At the level of analysis achieved it is not possible to exclude effects of the IS element and/or the adjacent deletion on the transcription of adjacent bacterial genes. Phage structural proteins interact with bacterial structures at least for phage adsorption and DNA injection. The apparent lack of intracellular phage DNA in the Sfi1-R7 and Sfi1-R71 mutants may be an indication of interference with phage DNA injection. In phages from Gram-positive bacteria initial phage adsorption and phage DNA injection seem to follow a two step process. First, phages adsorb reversibly to carbohydrate components of the cell wall, then appears to follow an irreversible interaction with the plasma membrane and ejection of DNA. For bacteriophage c2 it has been shown that a membrane protein, PIP, was responsible for irreversible phage adsorption to the host. Phage c2 was unable to infect cells with defective PIP proteins. Whether PIP is also responsible for phage DNA injection or other structures are needed is not known. For example, bacteriophage λ requires a host protein (Pel) in addition to the LamB receptor for an effective DNA injection. Pel is apparently not involved in phage adsorption since λ binds tightly to $E.$ $coli$ pet strains. It is thus possible that in the case of the Sfi1-R7 and Sfi1-R71 mutants, proteins involved in phage irreversible adsorption and/or DNA injection have been modified. In fact, the sequence information available for Sfi1-R7 indicates that the insertion of pG$^+$host9ISS1 may have blocked the expression of a putative integral membrane protein.

The phage resistance phenotype of Sfi1-R24 resembles that of an abortive infection mechanism. The phage DNA can enter the cell and phage DNA replication takes place, but it is delayed and diminished. In view of this it is considered that the insertion event affects the expression of a host factor involved in a phage multiplication step preceding DNA replication. Blockage of this step could affect DNA replication negatively. In the case of Sfi1-R24, the oxidoreductase is not the host factor whose inactivation causes the delay in DNA replication since its interruption by the IS element after plasmid excision fails to provide phage inhibition. Apparently, the transcription of adjacent genes is disturbed by the integrated plasmid. A gene encoding a subunit of a restriction endonuclease was the only bioinformatic bit in the targeted region. However, restriction and modification mechanisms are excluded since no traces of phage DNA degradation are detected in the Southern blot (FIG. 2). Direct interference with phage DNA replication is unlikely since the inhibited phages have apparently different DNA replication modules and are thus likely to depend on different host replication functions.

The Sfi21 prophage could be inactivated by targeted food-grade phage gene inactivation. No release of infectious particles by the Sfi1c16Δ1560 lysogen could be detected after prophage induction. Importantly, the inactivated prophage retained its protective effect against superinfection with a broad range of temperate and lytic $S.$ $thermophilus$ phages. Consequently, inactivated lysogens can now be considered as valuable starters. Their protective power exceeds that obtained with starter strains containing phage-inhibitory plasmids. For example, the superinfection immunity gene of Sfi21 (orf 203) was cloned in a high copy number plasmid and tested for protection against phages. It was quantitatively and qualitatively less complete than that mediated by the prophage. In addition, the plasmid was no longer phage inhibitory when integrated as a single copy into the bacterial chromosome. Therefore, the use of orf 203 has to rely on its presence on a high copy number plasmid, with the problem of high metabolic costs and plasmid instability. In contrast, the integrated prophage seems to be of low metabolic cost to the cell since lysogenic and non-lysogenic $S.$ $thermophilus$ starters have identical growth properties. Inactivated prophages can be used to increase the phage resistance of other strains than Sfi1 since a number of valuable industrial $S.$ $thermophilus$ starters can be lysogenized with phage Sfi21.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A *Streptococcus thermophilus* bacterium resistant to attack by at least one bacteriophage, said bacterium comprising at least one of the modifications selected from the group consisting of addition of DNA in ORF 90 of the bacterial chromosome sufficient to disrupt expression of the chorismate mutase chain A gene, and deletion of at least part of ORF 1560 of the genome of a φSfi21 prophage in the bacterium to disrupt expression of said φSfi21 prophage wherein the addition of DNA comprises bacterial insertion sequence (ISS1).

2. The bacterium according to claim 1 which is a modified bacterium of a strain of *S. thermophilus* selected from the group consisting of Sfi1 and Sfi1c16.

3. A composition comprising:
a *Streptococcus thermophilus* bacterial strain including at least one of the modifications selected from the group consisting of addition of DNA in ORF 90 of the bacterial chromosome sufficient to disrupt expression of the chorismate mutase chain A gene, and deletion of at least part of ORF 1560 of the genome of a φSfi21 prophage in the bacterial strain to disrupt expression of said φSfi21 prophage; and at least one component selected from the group consisting of a carrier, adjuvant and diluent.

4. A starter culture comprising a *Streptococcus thermophilus* bacterial strain including at least one of the modifications selected from the group consisting of addition of DNA in ORF 90 of the bacterial chromosome sufficient to disrupt expression of the chorismate mutase chain A gene, and deletion of at least part of ORF 1560 of the genome of a φSfi21 prophage in the bacterial strain to disrupt expression of said φSfi21 prophage.

5. The composition according to claim 3 wherein the bacterial strain is a modified bacterial strain of a strain of *S. thermophilus* selected from the group consisting of Sfi1 and Sfi1c16.

6. A milk product comprising a *Streptococcus thermophilus* bacterial strain including at least one of the modifications selected from the group consisting of addition of DNA in ORF 90 of the bacterial chromosome sufficient to disrupt expression of the chorismate mutase chain A gene, and deletion of at least part of ORF 1560 of the genome of a φSfi21 prophage in the bacterium to disrupt expression of said φSfi21 prophage.

7. The starter culture according to claim 4 wherein the bacterial strain is a modified bacterial strain of a strain of *S. thermophilus* selected from the group consisting of Sfi1 and Sfi1c16.

8. The milk product according to claim 6 wherein the bacterial strain is a modified bacterial strain of *S. thermophilus* selected from the group consisting of Sfi1 and Sfi1c16.

9. A *Streptococcus thermophilus* bacterial strain, wherein at least one of the bacterial chromosome or a φSfi21 phage genome of said strain is modified such that phage replication within the bacterium is prevented, wherein the modification is selected from the group consisting of addition of DNA to the bacterial chromosome in ORF 90 at a site which disrupts expression of the chorismate mutase chain A gene and deletion of DNA from at least part of ORF 1560 of the φSfi21 prophage to disrupt expression of said prophage.

10. The *S. thermophilus* bacterial strain according to claim 9, which is a modified bacterial strain of a strain of *S. thermophilus* selected from the group consisting of Sfi1 and Sfi1c16.

11. The composition according to claim 3 wherein the addition of DNA comprises bacterial insertion sequence (ISS1).

12. The starter culture according to claim 4 wherein the addition of DNA comprises bacterial insertion sequence (ISS1).

13. The milk product according to claim 6 wherein the addition of DNA comprises bacterial insertion sequence (ISS1).

14. The bacterial strain according to claim 9 wherein the addition of DNA comprises bacterial insertion sequence (ISS1)

* * * * *